United States Patent [19]

Zasloff

[11] Patent Number: 4,810,777

[45] Date of Patent: Mar. 7, 1989

[54] ANTIMICROBIAL COMPOUNDS

[75] Inventor: Michael A. Zasloff, Rockville, Md.

[73] Assignee: The United States of America as represented by the Department of Health and Human Services, Washington, D.C.

[21] Appl. No.: 21,493

[22] Filed: Mar. 4, 1987

[51] Int. Cl.[4] ........................... C07K 7/08; C07K 7/10

[52] U.S. Cl. ........................................ 530/326

[58] Field of Search ............... 530/324, 325, 326, 317, 530/842, 827, 326, 842; 514/21, 12, 13, 21

[56] References Cited

U.S. PATENT DOCUMENTS 4,195,018 3/1980 Takita et al. ........................ 530/322
4,409,210 10/1983 Kawaguchi et al. ............... 530/317

OTHER PUBLICATIONS

Williams, *Chemical & Engineering News*, Oct. 5, 1987.
Goldsmith, *Arch Dermatol*, 123:1087–1088, 1987.
Zasloff Proc. Natl. Acad. Sci. USA 84:5449–5453, 1987.
Giovannini et al., *Biochem. J.*, 243:113–120, 1987.
Csordas et al., *Toxicon* &;103–108, 1969.
Eisenberg, *Ann Rev. Biochem.* 53:595–623, 1984.
Kaiser et al., *Proc. Natl. Acad. Sci. USA* 80:1137–1143, 1983.
Sures et al., *Proc. Natl. Acad. Sco. USA* 81:380–384, 1984.
*CRC Handbook of Chemotherapeutic Agents* vol. I, pp. 178–185, "Peptide Antibiotics".
Kempf et al., *J. Biol. Chem.* 257:2469–2476, 1982.
Steiner et al., *Nature* 292:246–248, 1981.
Hoffmann et al., *Embo, J.* 2:711–714, 1983.
Andreu et al., *Biochem.* 149:531–535, 1985.
Merrifield et al., *Biochem.* 21:5020–5031, 1982.
Gibson et al., *J. Biol. Chem.* 261:5341–5349, 1986.
Richter et al., *Peptides* 6:17–21, 1985.

*Primary Examiner*—Delbert R. Phillips
*Assistant Examiner*—T. D. Wessendorf
*Attorney, Agent, or Firm*—Holman & Stern, Chartered

[57] ABSTRACT

A new class of broad spectrum antibiotic polypeptides termed "Magainin" have been described. These peptides have a molecular weight of about 2500 or less, are highly water soluble, non-cytolyic to animal cells including red-blood cells and are amphiphilic.

8 Claims, No Drawings

ANTIMICROBIAL COMPOUNDS

BACKGROUND OF THE INVENTION

The present invention relates generally to antimicrobial compounds. More particularly, the present invention is related to a new class of polypeptides, designated herein "Magainins", which have a broad range of antimicrobial activity. It is noted that the "Magainin" family of compounds having the properties as described herein have never heretofore been discovered or known.

SUMMARY OF THE INVENTION

It is, therefore, an object of the present invention to provide a novel family of compounds, termed "Magainins."

It is a further object of the present invention to provide a novel class of antibiotics providing effective defense against infection by such organisms as gram-positive and gram-negative bacteria, fungi, protozoan species and the like.

Various other objects and advantages will become apparent from the Detailed Description of the Invention.

DETAILED DESCRIPTION OF THE INVENTION

The above and various other objects and advantages of the present invention are achieved by Magainins which are defined as a class of polypeptides having a molecular weight of about 2500 or less, being water soluble at a concentration of greater than 5 mg per ml at neutral pH or in an aqueous solution of physiologic ionic strength, being non-cytolytic to animal cells including red blood cells, being amphiphilic and having a broad antibiotic spectrum at physiologic ionic strength and pH. Such polypeptides include Magainin I, Magainin II, Magainin III and analogs or derivatives thereof.

Table I shows the amino acid sequence (single letter code) of certain Magainin polypeptides of the present invention.

TABLE I

Primary Sequence of Magainin Polypeptides

Magainin I: $(NH_2)$GIGKFLHSAGKFGKAFVGEIMKS(OH)

Magainin II: $(NH_2)$GIGKFLHSAKKFGKAFVGEIMNS(OH)

Magainin III: $(NH_2)$GIGKFLHSAKKFGKAFVGEIMN(OH)

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

Of course, having described the amino acid sequence of the Magainins, these polypeptides can be routinely synthesized by standard techniques well known in the art, such as by commercially available peptide synthesizers and the like. Such standard techniques of polypeptide synthesis can be found described in such publications as *Merrifield,* J. Chem. Soc. 85: 2149–2154, 1963; *Hunkapillar et al,* Nature 310: 105–111, 1984.

It is noted, however, that the amino acid sequences of Magainins listed in Table I show only essential portions required for antibiotic activity. In otherwords, the polypeptides are not limited to the sequences shown in Table I, but must have, at least in part or in whole the amino acid sequence shown in Tables I and II. Of course, various analogs and derivatives of Magainins can be easily predicted, generated and/or prepared by such standard and common methods as NMR (Nuclear magnetic resonance), computer modeling and the like and all such analogs or derivatives which are equivalent in structure and function to the Magainins as defined herein are encompassed within the scope of the disclosure contained herein. Some derivatives of Magainin II and their antimicrobial activities, for instance, are shown in Table II. It is clear from the results presented in Table II that the Magainins could be manipulated, for example progressively made shorter at the amino terminus, and still retain antimicrobial potency.

Table III shows the antimicrobial spectrum of the synthetic Magainin peptides of the present invention.

TABLE II

| Derivative | Antimicrobial Activity of Truncated Synthetic Derivatives of Magainin II (Single Letter Code) | Zone of Inhibition on Lawn of *E. coli* Y1088 Generated by 50 μg of the Peptide (mm) |
|---|---|---|
| Magainin II(a) | $(NH_2)$IGKFLHSAKKFGKAFVGEIMNS(OH) | 10 |
| Magainin II(b) | $(NH_2)$GKFLHSAKKFGKAFVGEIMNS(OH) | 10 |
| Magainin II(c) | $(NH_2)$KFLHSAKKFGKAFVGEIMNS(OH) | 10 |
| Magainin II(d) | $(NH_2)$FLHSAKKFGKAFVGEIMNS(OH) | 2 |
| Magainin II(e) | $(NH_2)$LHSAKKFGKAFVGEIMNS(OH) | 1 |
| Magainin II(f) | $(NH_2)$HSAKKFGKAFVGEIMNS(OH) | 0 |

TABLE III

Antimicrobial Spectrum of Synthetic Magainin Peptides

| Organism(ATCC) | Magainin I | Magainin II | Magainin III |
|---|---|---|---|
| | (Minimal Inhibitory Concentration (μg/ml)) | | |
| *Eschericia coli* D31 | 1–20 | 1–10 | 1–10 |
| *Acinetobacter caloaceticus*(19606) | 7–35 | 1–7 | 7–35 |
| *Shigella sonnei* (25931) | 7–35 | 1–7 | 7–35 |
| *Enterobacter sonnei* (23355) | 7–35 | 1–7 | 7–35 |
| *Eschericia coli* (25922) | 7–35 | 1–7 | 7–35 |
| *Streptococcus pyogenes* (19615) | 7–35 | 1–7 | 7–35 |
| *Shigella flexneri* (12022) | 35–70 | 7–35 | 7–35 |
| *Citrobacter freundii* (8090) | >100 | 7–35 | 7–35 |
| *Enterobacter* | >100 | 7–35 | >100 |

TABLE III-continued

| Antimicrobial Spectrum of Synthetic Magainin Peptides | | | |
|---|---|---|---|
| Organism(ATCC) | Magainin I | Magainin II | Magainin III |
| *aerogenes* (13048) | | | |
| *Klebisiella pneumonia* (13883) | >100 | 7-35 | >100 |
| *Staphyloccus epidermidis* (1228) | >100 | 7-35 | 35-70 |
| *Streptococcus faecalis* (19433) | >100 | 35-70 | >100 |
| *Pseudomonas aeruginosa* (27853) | >100 | 35-70 | 35-70 |
| *Salmonella typhimurium* (14028) | >100 | 35-70 | 35-70 |
| *Staphylococcus aureus* (25923) | >100 | 35-70 | >100 |
| *Candida albicans* (14053) | >100 | 35-70 | >100 |
| *Proteus vulgaris* (13315) | >100 | >100 | >100 |
| *Serratia marcescens* (8100) | >100 | >100 | >100 |

TABLE IV

| Antiprotozoan Activity of Synthetic Magainin Peptides | | | |
|---|---|---|---|
| Organism | Magainin I | Magainin II | Magainin III |
| (Concentration required for osmotic lysis (μg/ml)) | | | |
| *Paramecium caudatum* | 5 | 5 | 5 |
| *Amoeba proteus* | 5 | 5 | 5 |
| *Euglena gracilis* | 5 | 5 | 5 |

Table III also lists the range of minimal inhibitory concentrations for various organisms assayed in trypticase soy broth. These determinations were made following standard techniques well known in the art and described in such publications as, DIFCO Manual, 10th edition, 1984, pages 78-80.

Table IV lists the approximate concentration of Magainins which induces physical lysis of several representative protozoan species. These determinations were made by visual assessment of the treated organisms by light microscopy. Of course, the optimal effective antimicrobial concentration of a particular Magainin can be easily determined in a routine manner without undue expermentation by techniques well known to one of ordinary skill in the art.

It is clear from the results presented in Tables III and IV that the Magainin polypeptides of the present invention have a broad range of potent antibiotic activity against a plurality of microorganisms including gram-positive and gram-negative bacteria, fungi, protozoa and the like. Hence it is apparent that the Magainin antibiotics of the present invention allow a method of treating or controlling microbial infection caused by those organisms which are sensitive to Magainin. Such treatment comprises administering to a host or tissue susceptible to or afflicted with microbial infection an antimicrobial amount of Magainin.

Clearly, due to their antibiotic properties, the Magainins of the present invention can also be used as preservatives or sterilants of materials susceptible to microbial contamination.

Of course, pharmaceutical compositions comprising Magainin polypeptides of the present invention as an active ingredient in an amount sufficient to produce antibiotic effect in suseptible host or tissue and a pharmaceutically acceptable, non-toxic sterile carrier can be easily prepared based on the data provided herein. Such carriers could be fillers, non-toxic buffers, physiological saline solution and the like. The preparation can be used topically or systemically and may be in any suitable form such as liquid, solid or semi-solid, which include injectable solutions, tablets, ointments, lotions, pastes, capsules and the like. Of course, the Magainins may also be administered in combination with other adjuvants, protease inhibitors, or compatible drugs where such combination is seen desirable or advantageous in controlling the infection caused by harmful microorganisms including protozoa, viruses and the like.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An antibiotic having an amino acid sequence of: $(NH_2)$GIGKFLHSAGKFGKAFVGEIMKS(OH).

2. An antibiotic having an amino acid sequence of: $(NH_2)$GIGKFLHSAKKFGKAFVGEIMNS(OH).

3. An antibiotic having an amino acid sequence of: $(NH_2)$GIGKFLHSAKKFGKAFVGEIMN(OH).

4. An antibiotic having an amino acid sequence of: $(NH_2)$IGKFLHSAKKFGKAFVGEIMNS(OH).

5. An antibiotic having an amino acid sequence of: $(NH_2)$GKFLHSAKKFGKAFVGEIMNS(OH).

6. An antibiotic having an amino acid sequence of: $(NH_2)$KFLHSAKKFGKAFVGEIMNS(OH).

7. An antibiotic having an amino acid sequence of: $(NH_2)$FLHSAKKFGKAFVGEIMNS(OH).

8. An antibiotic having an amino acid sequence of: $(NH_2)$LHSAKKFGKAFVGEIMNS(OH).

* * * * *